(12) United States Patent
Oda

(10) Patent No.: US 6,606,154 B1
(45) Date of Patent: Aug. 12, 2003

(54) SAMPLE INSPECTING APPARATUS

(75) Inventor: Tatefumi Oda, Aichi (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 09/350,122

(22) Filed: Jul. 9, 1999

(30) Foreign Application Priority Data

Jul. 10, 1998 (JP) ............................................. 10-195850

(51) Int. Cl.[7] .............................................. G01N 21/01
(52) U.S. Cl. ................................... 356/244; 356/237.5
(58) Field of Search .......................... 356/244, 237.5; 414/754; 248/542

(56) References Cited

U.S. PATENT DOCUMENTS

| | | | | |
|---|---|---|---|---|
| 4,887,904 A | * | 12/1989 | Nakazato et al. ............ | 356/373 |
| 5,052,886 A | * | 10/1991 | Moroi ........................ | 414/757 |
| 5,502,799 A | * | 3/1996 | Tsuji et al. ................. | 395/131 |
| 6,204,917 B1 | * | 3/2001 | Smedt ....................... | 356/237.5 |

FOREIGN PATENT DOCUMENTS

| | | |
|---|---|---|
| JP | 6378258 | 5/1988 |
| JP | 6-349908 | 12/1994 |
| JP | 7229837 | 8/1995 |
| JP | 10-92887 | 4/1998 |
| JP | 10-116869 | 5/1998 |

\* cited by examiner

*Primary Examiner*—Frank G. Font
*Assistant Examiner*—Layla Lauchman
(74) *Attorney, Agent, or Firm*—Finnegan, Henderson, Farabow, Garrett & Dunner, L.L.P.

(57) ABSTRACT

A sample inspecting apparatus which performs a visual inspection of a sample to be inspected by reflected light therefrom, the apparatus comprising holding device which holds the sample at its periphery, first rotating device which rotates the holding device on a first axis passing through an approximate center of the sample being held by the holding device and second rotating device which rotates the holding device on a second axis passing through the approximate center of the sample being held by the holding device.

7 Claims, 5 Drawing Sheets

SAMPLE INSPECTING APPARATUS

BACKGROUND OF THE INVENTION

1. Field of the Invention

The present invention relates to a sample inspecting apparatus for inspecting a sample typified by a semiconductor wafer. More specifically, the present invention relates to a macro inspection mechanism of the sample inspecting apparatus which is suitable for a visual inspection of a sample, in particular both back and front surfaces of the sample.

2. Description of Related Art

A semiconductor wafer having a predetermined pattern formed thereon goes through inspections which are roughly divided into two. One is a macro inspection which is a visual inspection by an inspector for presence or absence of scratches or dust. The other is a micro inspection which is an inspection, with a microscope, of a state of the pattern formed on the surface.

Generally in the macro inspection of a semiconductor wafer, a wafer is illuminated by illumination light thereby to visually inspect the reflected light therefrom for inconsistencies in color, scratches, dust and the like. Upon this type of inspection, conventionally, a semiconductor wafer is adsorbed and held by a macro stage, and then the macro stage is rotated or inclined so as to change the state of the wafer surface for the visual inspection. In recent years, it has been more and more general to enlarge a wafer diameter and to fine its pattern. As a result, small dust which has been overlooked without any problems in the past may cause deficiency, and therefore problems associated with dust are getting more difficult.

Also, flatness of a back surface of the wafer has come to greatly influence the state of pattern, so that more importance has been attached to the necessity for inspecting the back surface of the wafer. One suggested apparatus for this type of inspection is provided with a wafer holding part, apart from a front surface inspection mechanism, which adsorbs or holds the wafer by the periphery to lift the wafer to a position where the inspector can observe the back surface of the wafer (see FIG. 6). This type of inspecting apparatus operates to place the wafer on a macro stage once to perform the front surface inspection, and then to release the adsorption by the macro stage. Thereafter the wafer holding part lifts the wafer.

However, the conventional macro inspecting apparatus has the following problems.

(a) In the mechanism which adsorbs and holds the back surface of the wafer, the wafer has contact with the adsorptive surface. This results in a possibility of adhesion of dust.

(b) The mechanism which lifts the wafer with the wafer holding part by adsorbing and holding upon the back surface inspection also has a possibility that dust may adhere to the back surface of the wafer. In addition, portion of the wafer where the wafer holding part adsorbs the wafer is obstructed. In short, the disadvantage is that there is an uninspected portion is left and the portion can not be inspected.

(c) The mechanism which lifts the wafer with the wafer holding part to perform the back surface inspection disadvantageously provides an inspector different points of view between the front surface inspection and the back surface inspection. For this reason, stable and accurate inspections can not be performed.

(d) In the front surface inspection, it is possible to rotate or incline the wafer with the macro stage to allow inspection from various angles. In the back surface inspection, however, the wafer is held still with the wafer holding part during the inspection. Therefore, the inspection is performed only at one specific angle to be insufficient.

(e) In a macro inspection, the wafer is illuminated and the inspection is performed using the reflected light therefrom. To deal with the different positions of the wafer upon the front surface inspection and the back surface inspection, illumination units need to be provided at suitable positions for each inspection.

SUMMARY OF THE INVENTION

The present invention has been made in view of the above circumstances and has an object to overcome the above problems and to provide a sample inspecting apparatus which is capable of reducing adhesion of dust to the back surface of the wafer and of stably performing the front surface inspection as well as the back surface inspection under the even conditions.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, a sample inspecting apparatus of this invention which performs a visual inspection of a sample to be inspected by reflected light therefrom, the apparatus comprises holding means which holds the sample at its periphery, first rotating means which rotates the holding means on a first axis passing through an approximate center of the sample being held by the holding means and second rotating means which rotates the holding means on a second axis passing through the approximate center of the sample being held by the holding means.

In another aspect of the present invention, a sample inspecting apparatus of this invention which performs a visual inspection of a sample to be inspected by reflected light therefrom, the apparatus comprises a holder which holds the sample at its periphery, first rotation mechanism which rotates the holder on a first axis passing through an approximate center of the sample being held by the holder and second rotation mechanism which rotates the holder on a second axis passing through the approximate center of the sample being held by the holder.

As described, according to the present invention, a sample such as a wafer can be placed in the same position under the same condition in the front surface inspection and the back surface inspection. This eliminates the necessity that the inspector changes his point of view for each inspection.

In addition, it also eliminates the necessity to provide different illumination units for the front surface inspection and the back surface inspection or to move one illumination unit upon each inspection. Therefore, the inspection can be performed efficiently.

Further, since it is unnecessary to switch the hold of the wafer upon inspecting the front surface and the back surface of the sample, the inspection can carry out smoothly.

Still further, the inspection of both surfaces of the sample may be performed without adapting a mechanism to adsorb the sample. Accordingly, the inspection can be performed without leaving an uninspected part upon the back surface inspection and contamination by dust can be reduced as well.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
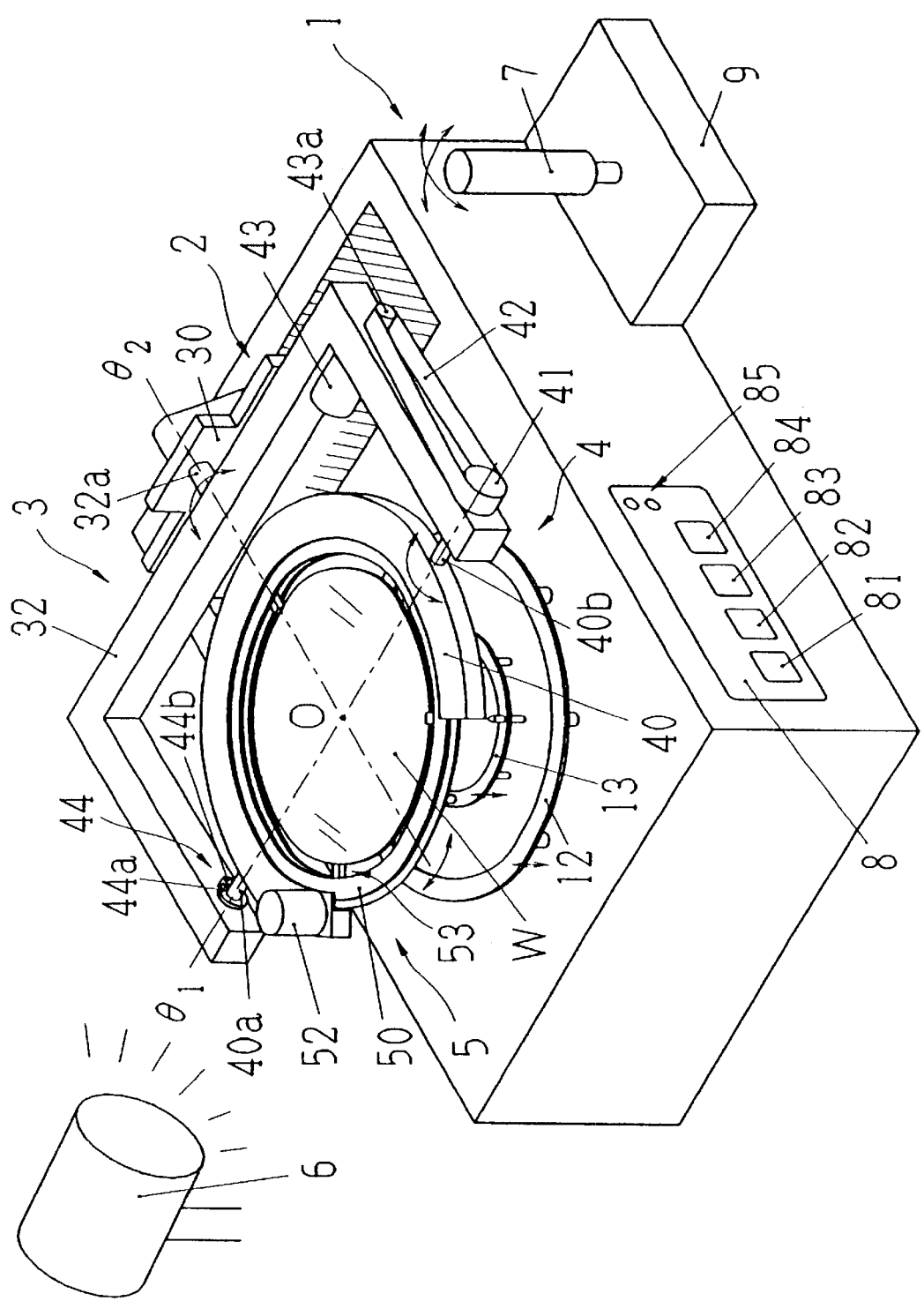
FIG. 1 is a schematic view showing an external representation of a sample inspecting apparatus embodying the present invention.

A detailed description of one preferred embodiment of a sample inspecting apparatus embodying the present invention will now be given referring to the accompanying drawings. FIG. 1 is a schematic view showing an external representation of the sample inspecting apparatus for a visual inspection of a semiconductor wafer.

Main body 1 is provided with: a rotation unit 5 which holds a wafer W to rotate on a rotation center O within its plane; a right and left inclination unit 4 which inclines (rotates) the rotation unit 5 toward right and left (as seen from a side to which a joystick 7, described later, is arranged) with an axis θ1 passing through the rotation center O as its center; a back and forth inclination unit 3 which inclines (rotates) the right and left inclination unit 4 toward back and forth with an axis θ2 passing through the rotation center O as its center; and a vertical motion unit 2 which vertically moves the back and forth inclination unit 3. Provided vertically movably on the housing of the main body 1 is a ring 12 which effects holding and releasing of the wafer W by the rotation unit 5 as well as a wafer stage 13 which is used to place the wafer W on the rotation unit 5.

6 is an illumination unit which illuminates the wafer w upon the macro inspection. Depending on the inspection process, various kinds of filters (green, yellow, polarizing plate, or the like) may be selectively added and used.

7 is the joystick for freely inclines the wafer W held by the rotation unit 5. An encoder arranged in a box 9 detects information on the inclination made by the joystick 7. Based on the information detected thereby, the back and forth inclination unit 3 and the right and left inclination unit 4 are driven.

8 is an operation panel provided with a start switch 81 to start the inspection, a pass switch 82 and a fail switch 83 to make accept or reject judgement, a reverse switch 84 to reverse the wafer W to the other side, and inspection surface display LEDs 85 to respectively indicate the front or back surface of the wafer W being inspected.

Figure 2:
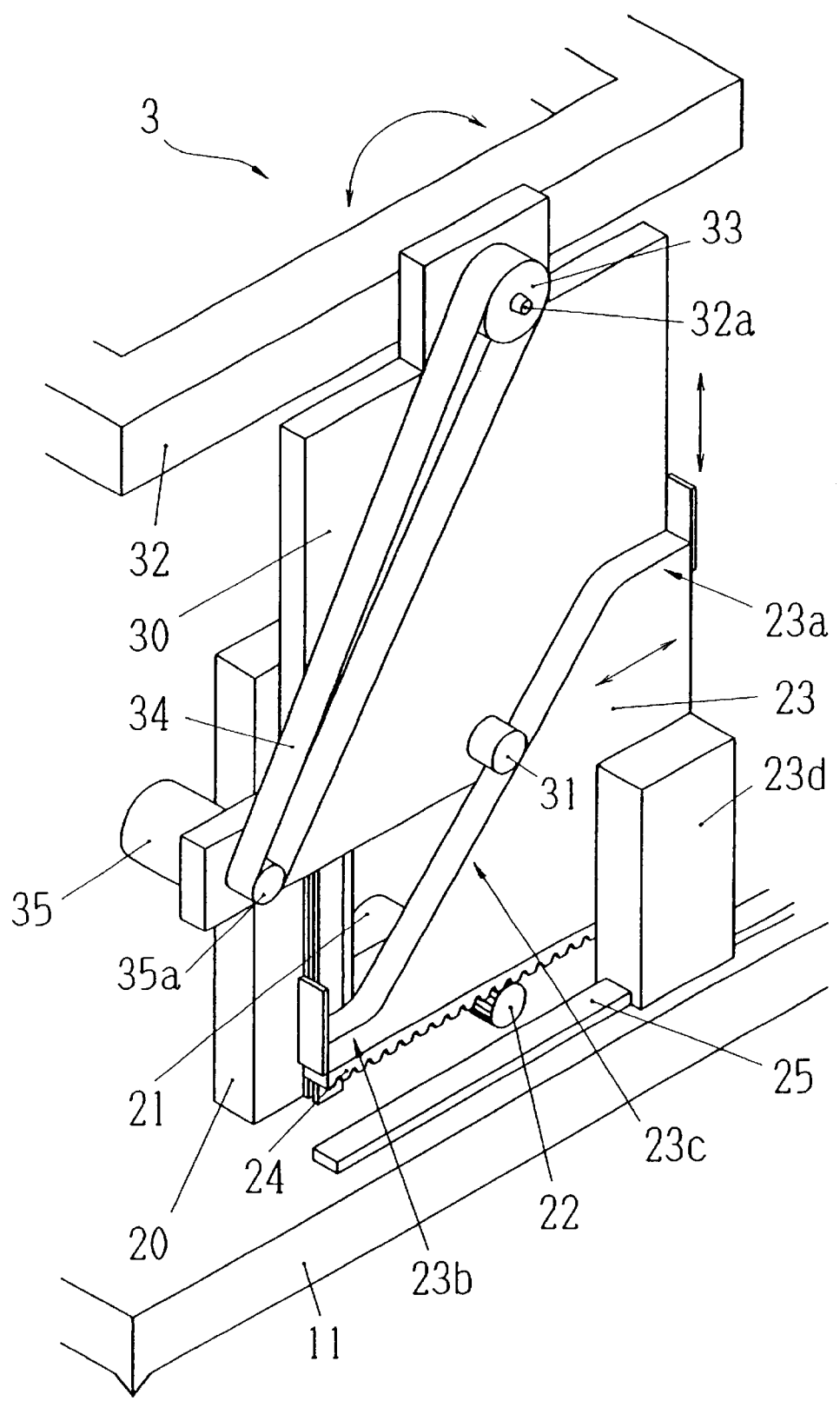
FIG. 2 is a schematic view showing a mechanism of a vertical motion unit and a back and forth inclination unit of the sample inspecting apparatus.
Figure 3:
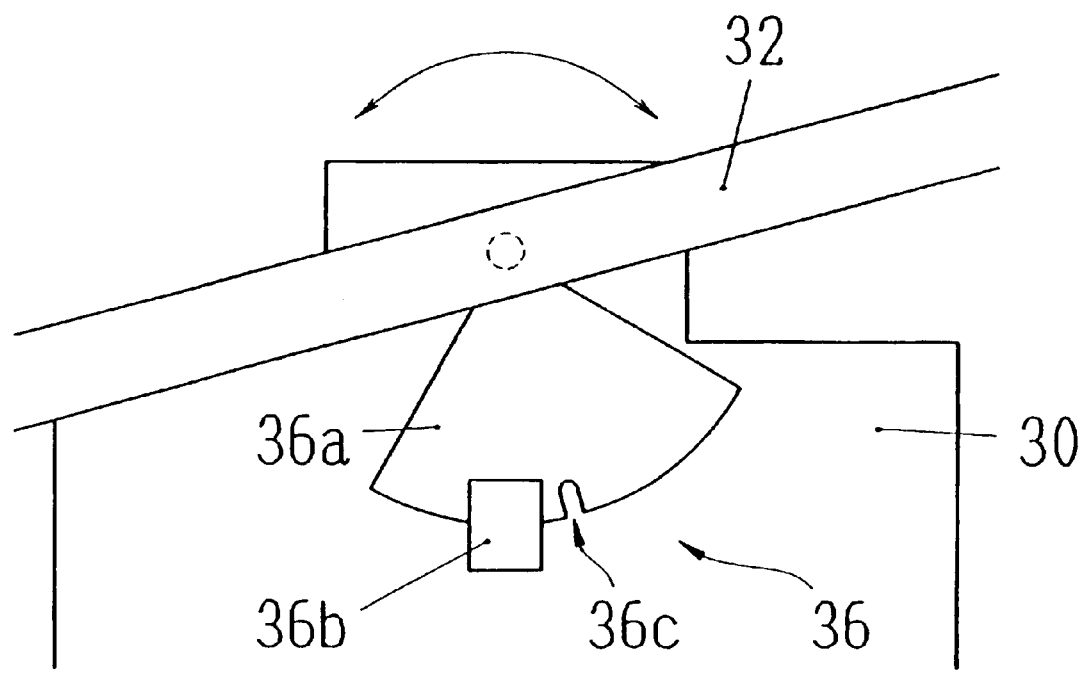
FIG. 3 is a schematic view showing a mechanism to detect an initial inclined position of the sample inspecting apparatus.

Hereinafter, description is given to configuration of each unit which makes rotation of the wafer and other operations with reference to FIGS. 1–4. FIG. 2 is a view showing a mechanism of the vertical motion unit 2 and the back and forth inclination unit 3. FIG. 3 is a view showing a mechanism to detect an initial inclined position of the back and forth inclination unit 3. FIG. 4 is a view showing the wafer holding mechanism of the rotation unit 5.

Vertical Motion Unit

As shown in FIG. 2, a base 20 is vertically fixed to a base 11 that the main body 1 has and a vertical motion base 30 is held slidably in a vertical direction along the base 20. 23 is a vertical motion cam to produce vertical movements of the base 30. The cam 23 is movable in a back and forth direction along a guide 25 by a block 23d. A rack 24 is provided at the lower edge of the cam 23 and a gear 22 mounted at the end of the rotation shaft of a DC motor 21 engages the rack 24. The cam 23 moves in a back and forth direction by the rotation of the motor 21. Formed at the upper edge of the cam 23 are horizontal end faces 23a and 23b at different heights, and also a sloping end face 23c providing a smooth connection therebetween. A roller 31 mounted on the vertical motion base 30 is arranged in engagement against the end faces 23a, 23b, and 23c. Because of the above configuration, the rotation of the motor 21 produces the back and force movement of the cam 23. As the cam 23 moves, the vertical motion base 30 moves up and down via the roller 31.

Back and Forth Inclination Unit

The back and forth inclination unit 3 is comprised of the following main components; two swinging arms 32, a toothed pulley 33, a toothed belt 34, a pulse motor 35 and a sensor unit 36 for detecting an initial position (see FIG. 3).

The vertical motion base 30 is provided with the motor 35 fixedly mounted at the lower part thereof, and with the arms 32 rotatably mounted via a shaft 32a at the upper part thereof. The shaft 32a is arranged so that its axial line (axis θ2) passes the rotation center O of the rotation unit 5 which rotates the wafer W. The pulley 33 is mounted to the shaft 32a and a toothed pulley 35a is provided at the end of the rotation shaft of the motor 35. The belt 34 that runs therebetween transfers the rotation driving force produced by the motor 35 to the pulley 33 to rotate (incline) the arms 32 on the shaft 32a.

Provided on the other side of the vertical motion base 30 from the pulley 33 is the sensor unit 36, as shown in FIG. 3, comprising a cover plate 36a, which rotates with the arms 32 and a sensor 36b, which is fixed to the vertical motion base 30. A notch 36c is formed in the cover plate 36a and the sensor 36b detects the position thereof to find out the initial position of the rotation.

Right and Left Inclination Unit

The right and left inclination unit 4 is comprised of the following main components; a rotation ring holding part 40, a toothed pulley 41, a toothed belt 42, a pulse motor 43 and a sensor unit 44.

As shown in FIG. 1, the holding part 40, which rotatably holds a rotation ring 50, is mounted at the end of the arms 32 with shafts 40a and 40b on each arm in a manner to be rotatable on an axial line (axis θ1) along which the shafts 40a and 40b coincide with each other. The axis θ1 is arranged so as to pass the rotation center O of the rotation unit 5. That is, the axis θ1 is parallel to the surface of the wafer W being held by the rotation unit 5 and passes its approximate center. The pulley 41 mounted to the shaft 40b is, via the belt 42, in connection with the pulley 43a of the motor 43 which is fixed on one of the arms 32 near the base 30. Due to this configuration, the rotation driving force produced by the motor 43 is transferred to the pulley 41 via the belt 42 thereby to rotate the holding part 40 on the axis θ1.

On the side of the shaft 40a, the sensor unit 44 is provided. Similar to the above-described sensor unit 36, the sensor unit 44 comprises a cover plate 44a, which rotates with the holding part 40 and a sensor 44b, which is fixed to the one of the arm 32. The sensor 44b detects a notch formed in the cover plate 44a to find out the initial position of the rotation.

Rotation Unit

The rotation unit 5 is composed of the following main components; the rotation ring 50, rotation ring holding rollers 51 (see FIG. 4), a pulse motor 52, and chuck units 53 for holding the wafer.

Mounted to the holding part 40 at 120° intervals are the three rollers 51, with which the ring shaped rotation ring 50 is rotatably held. One of the rollers 51 is mounted to the rotation shaft of the motor 52 which is fixed to the holding part 40, and therefore, the rotation of the motor 52 causes the rotation of the rotation ring 50 being held by the holding part 40 on the rotation center O.

Figure 4A:
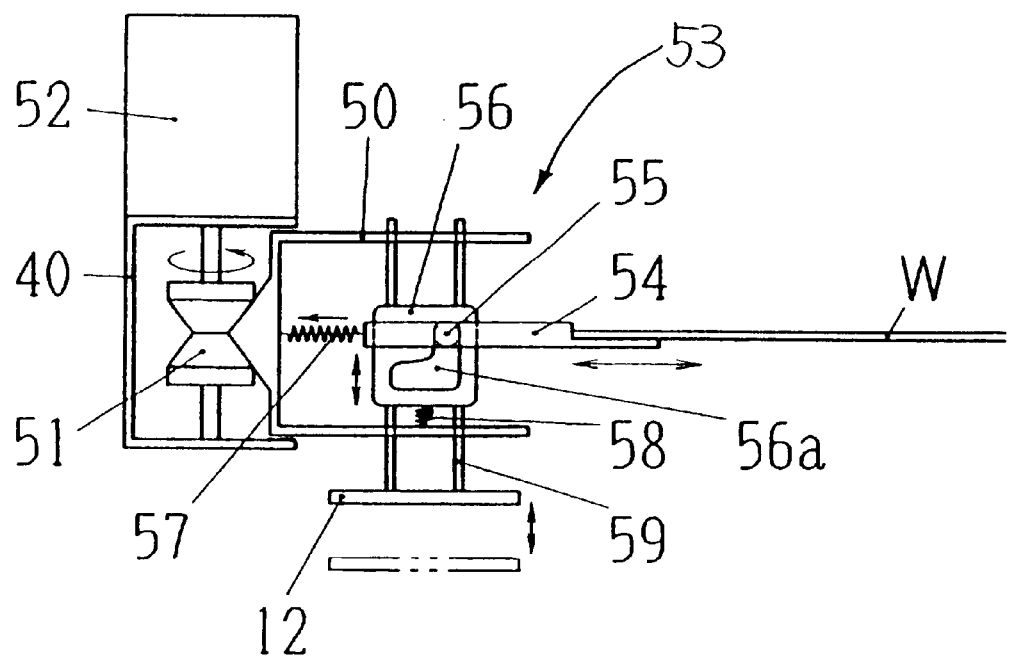
FIGS. 4A and 4B are schematic views showing a wafer holding mechanism of the sample inspecting apparatus.

The rotation ring 50 is provided with the three chuck units 53 at 120° intervals for holding the wafer W at its periphery with three points. As shown in FIG. 4A, each of the chuck units 53 consists of a chuck 54 provided with an L-shaped wafer receiver, a guide pin 55 provided to the chuck 54, a guide plate 56 in which an approximate L-shaped ditch 56a is formed, and springs 57 and 58.

The chuck 54 is exerted the force by the spring 57 pulling in a centrifugal direction relative to the rotation center O. Also, the guide pin 55 is fixed to the chuck 54 and the guide pin 55 is in engagement with the guide ditch 56a formed in the guide plate 56. The guide plate 56 is pulled downward by the spring 58. Mounted at the lower edge of the guide plate 56 are two pins 59. When the ring 12 provided on the housing of the main body 1 is raised, the pins 59 will engage thereagainst and then the guide plate 56 is pressed up with resisting the force of the spring 58. As the guide plate 56 is pressed up, the guide pin 55 is allowed to move along the guide ditch 56a so that the chuck 54 being pulled in the centrifugal direction by the spring 57 moves in the direction to release the holding of the wafer W. Yet, the movement of the chuck 54 in the centrifugal direction is to such an extent that the wafer W does not fall even after the holding is released.

When the ring 12 is lowered, on the contrary, the force of the spring 58 brings down the guide plate 56 relative to the ring 50. As the result, the chuck 54 together with the guide pin 55 moves along the guide ditch 56a in the direction of the rotation center O thereby to hold the wafer W.

Figure 4B:
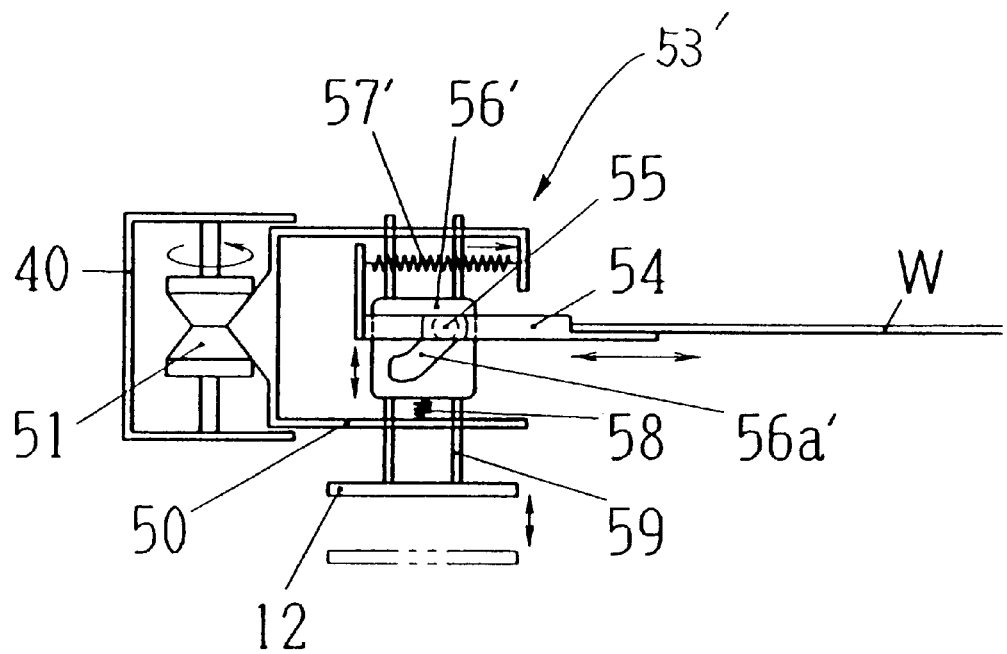

As shown in FIG. 4B, one of the three chuck units 53 is provided with a guide plate 56' in which a guide ditch 56a' different from the other ditches is formed, and a spring 57' with the force pulling in the direction of the rotation center O at all times. When the guide plate 56' is pressed up by the ring 12, this chuck unit 53', with resisting the force of the spring 57', moves along the guide ditch 56a' in the centrifugal direction. When the ring 12 is lowered (at the time of holding the wafer), the spring 57' constantly exerts the force pulling in the direction of the rotation center O. Due to this force, the wafer W does not fall even when the rotation unit 5 is rotated to turn the back surface of the wafer W up.

Figure 5:
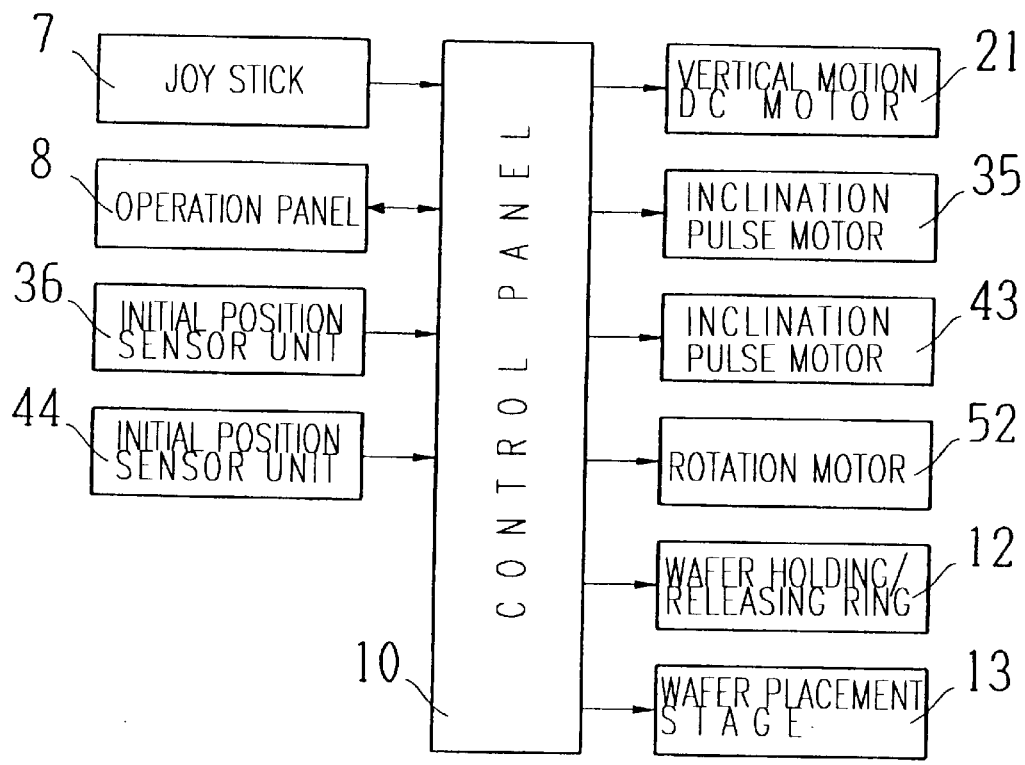
FIG. 5 is a block diagram showing an important part of a control system of the sample inspecting apparatus.
Figure 6:
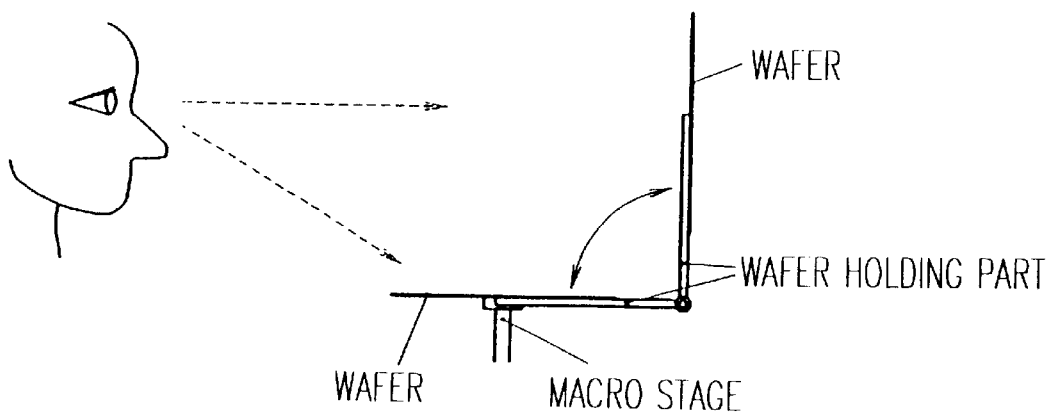
FIG. 6 is a view showing a conventional back surface inspecting apparatus.

Hereinafter, description is given to operations of the apparatus having above-described configuration with reference to FIG. 5 showing an important configuration of the control system of the apparatus.

The wafer W stored in a carrier or the like is transported by a wafer transporting device, not shown and then laid on the three chucks 54 provided to the rotation ring 50 with the use of the stage 13. When the wafer W is laid in place, the arms 32 and the rotation ring 50 are respectively in the horizontal state which are their initial positions as well as being descent to allow placement of the wafer W on the chucks 54.

Upon placing the wafer W, the stage 13 is elevated to a higher level than the rotation ring 50 and the wafer W transported by the wafer transporting device is temporarily placed on the stage 13. The stage 13 is provided with a protrusions for holding the wafer W in a manner of three-point holding so as to minimize a contact surface therebetween. More precisely, the wafer W is temporarily place on these protrusions. When the wafer W is placed on the stage 13, the control unit 10 lowers the stage 13 until it comes to a lower height than the rotation ring 50. When the stage 13 comes to an equal height to the rotation ring 50, the wafer will be automatically passed to and placed on the chucks 54.

When the wafer W is placed on the chucks 54, the control unit 10 lowers the ring 12. As the result, the chucks 54 moves toward the center of the wafer along the guide plate 56 thereby to hold the wafer W.

When the inspector depresses the start switch 81, the control unit 10 drives the motor 21 to elevate the back and force inclination unit 3 so as to move the wafer W up to an inspection position. When the wafer W is brought to the inspection position, the control unit 10 drives the motor 52 to rotate the rotation ring 50 together with the wafer W within the plane.

As the inspector operates the joy stick 7, the control unit 10, in response to operation a signal issued thereby, drives and controls the motor 35 to effect the back and force inclination of the arms 32 as well as the motor 43 to effect the right and left inclination of the rotation ring 50. This enables to incline the wafer W at any intended angel with respect to the rotation center O being its inclination center. While operating the joy stick 7 to change the inclination angle freely, the inspector observes the reflected light from the wafer W illuminated by the illumination unit 6 and performs the visual inspection of the front surface. During this operation, one of the display LEDs 85 indicating the front surface is being lit.

After the inspection of the front surface, the inspector determines whether to accept or reject the wafer W. The inspector, if accepts the wafer, depresses the pass switch 82 and goes on to the back surface inspection. (If the fail switch 83 is depressed, the unillustrated wafer transporting device receives the wafer W from the chuck units 53 with the use of the stage 13 and transports it to a carrier for rejected wafers). At the input of a signal issued in response to the pass switch 82, the control unit 10 rotates the holding part 40 180° by driving the motor 43 so as to place the wafer W with its back surface up. The wafer W rotates on the axis θ1 passing along its approximate plane, which allows the inspector to inspect the back surface of the wafer W under the substantially equal condition as the front surface inspection. Simultaneously with reversing the wafer W, the control unit 10 lights up the other display LEDs 85 indicating the back surface in order to inform the inspector that the back surface inspection is under way.

Upon the back surface inspection, in the like manner with the front surface inspection, the inspector operates the joy stick 7 to freely change the inclination angle of the wafer W. Simultaneously, the inspector observes the reflected light from the wafer W illuminated by the illumination unit 6 and then depresses either the pass switch 82 or the fail switch 83.

At input of the signal generated in response to the pass switch 82, the control unit 10 again rotates the motor 43 180° to place the wafer W with the front surface up. Further, the control unit 10 drives each motor based on the signals from the sensor units 36 and 44 to bring each unit back to their initial positions and then stops each unit with the wafer W being held horizontally. Thereafter, the control unit 10 drives the motor 21 to lower the wafer W. When the wafer W is brought down to its initial position where the wafer W is passed or received, the ring 12 elevates so that the holding by the chuck units 53 is released. When the holding is released, the stage 13 elevates to bring the wafer W to a higher level than the rotation ring 50. After having been placed on the stage 13 temporally, the wafer W is transport by the wafer transporting device to the wafer carrier or an inspection position for a micro inspection. In the case of receiving a signal generated in response to the fail switch 83, the control unit 10 make the same operations as above but transports the wafer W to the carrier for rejected wafers.

In the above description, the wafer W is reversed when the judgement switches 82 or 83 is depressed in the procedures of the front surface inspection or the back surface inspection. However, it is also possible to reverse the wafer W at any intended time by depressing the reverse switch 84.

In addition, the wafer W may be reversed for the back surface inspection by making the arms 32 rotatable more than 180°.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A wafer inspecting apparatus for performing a visual inspection of a wafer in light reflected therefrom, the apparatus comprising:
   a wafer holder including a ring-shaped first holder for holding a wafer to be inspected at its periphery with at least three chuck units that contact an edge and a back surface of the wafer and a second holder rotatably holding the first holder;
   a first rotatable shaft fixed to the wafer holder and rotatable on a first axis, the first axis passing through an approximate center of the wafer being held by the wafer holder and being approximately parallel to a plane of the held wafer;
   a shaft holder for rotatably holding the first shaft and movable between a wafer delivery position and a wafer inspection position; and
   a second rotatable shaft fixed to the shaft holder and rotatable on a second axis, the second axis passing through the approximate center of the wafer being held by the wafer holder and being approximately parallel to the plane of the held wafer.

2. The wafer inspecting apparatus according to claim 1, wherein the first and second shafts are rotatable 180° or more.

3. The wafer inspecting apparatus according to claim 1, wherein the first axis and the second axis cross each other at right angles.

4. The wafer inspecting apparatus according to claim 1, further comprising:
   a first motor for rotating the first shaft; and
   a second motor for rotating the second shaft.

5. The wafer inspecting apparatus according to claim 1, further comprising:
   a third motor for rotating the first holder with respect to the second holder.

6. The wafer inspecting apparatus according to claim 1, further comprising at least one of a first sensor unit for detecting an initial position of rotation of the first shaft and a second sensor unit for detecting an initial position of rotation of the second shaft.

7. The wafer inspecting apparatus according to claim 1, further comprising an illumination unit for illuminating the wafer from a predetermined direction.

\* \* \* \* \*